United States Patent [19]

Balazs

[11] 4,272,522

[45] Jun. 9, 1981

[54] METHOD FOR STIMULATING PHAGOCYTIC ACTIVITY AND SYNERGISTIC COMPOSITIONS THEREFOR

[76] Inventor: Endre A. Balazs, 3333 H. Hudson Pkwy., Riverdale, N.Y. 10463

[21] Appl. No.: 84,615

[22] Filed: Oct. 15, 1979

[51] Int. Cl.³ .............................................. A61K 37/62
[52] U.S. Cl. ...................................................... 424/94
[58] Field of Search ........................................... 424/94

[56] References Cited

U.S. PATENT DOCUMENTS 4,141,973   2/1979   Balazs .................................. 424/180

OTHER PUBLICATIONS

Wright et al., Chem. Abstracts, vol. 77(3), 18000z, Jul. 17, 1972.
Kusuda et al., Chem. Abstracts, vol. 77(6), 39,194f, Aug. 7, 1972.
Klockars et al., Chem. Abstracts, vol. 84(19), 133,551m, May 10, 1976.
Brandt et al., Chem. Abstracts, vol. 82(1), 2373r, Jan. 6, 1975.
The Merck Index, Ninth Edition, p. 733, item No. 5460, (1976).

*Primary Examiner*—Alan L. Rotman
*Attorney, Agent, or Firm*—Sheldon Palmer; Peter L. Berger

[57] ABSTRACT

Phagocytosis is enhanced or stimulated by injection of a mixture of a soluble hyaluronic acid salt and muramidase in amounts sufficient to achieve a blood level of each in the range of 10–15 $\mu$g/ml.

6 Claims, No Drawings

METHOD FOR STIMULATING PHAGOCYTIC ACTIVITY AND SYNERGISTIC COMPOSITIONS THEREFOR

BACKGROUND OF THE INVENTION

1. Field of the Invention

The present invention relates to methods of stimulating phagocytic activity and compositions therefor.

2. The Prior Art

A considerable amount of work has heretofore been done in connection with the natural phenomenon known as phagocytosis, in terms of attempting to understand the mechanism as well as attempting to enhance, or stimulate the process. It is, for example, known that hyaluronic acid (HA) and particularly the sodium salt thereof (Na-HA) both inhibits and stimulates phagocytosis, depending on conditions. Thus, Forrester and Balazs (1979) in Inhibition of phagocytosis by high molecular weight hyaluronate. (Submitted for, but not yet published); and Sebag, Balazs, Eakins, Bhattacherjee, and Kulkarni, (1979), in The effect of hyaluronic acid on prostaglandin synthesis and phagocytosis by mononuclear phagocytes in vitro, (Submitted for publication to The Journal of Cell Biology.) have shown that sodium hyaluronate (Na—HA) of various molecular sizes ($480-2300 \times 10^3$) inhibits the phagocytic activity of peritoneal macrophages. This inhibition depends on the viscosity of the solution to which the cells are exposed. Complete inhibition of phagocytosis of plastic beads was found to occur when the medium had a specific viscosity of 8 to 9. (Balazs, The effects of viscosity on phagocytosis [unpublished data].) This inhibition was not specific to Na-HA because gelatin and DNA solutions of approximately the same viscosity also caused complete inhibition. Sulfated glycosaminoglycans, however, in similar and even somewhat higher concentrations, and the oligosaccharides of HA did not cause inhibition, nor did they show interference with the inhibition of the higher molecular weight Na-HA.

Brandt, in The effect of synovial hyaluronate on the ingestion of monosodium urate crystals by leucozytes. Clinica Chimica Acta 55, 307-315 (1974), showed that various molecular weight Na-HA preparations ($2.94-0.86 \times 10^6$) inhibit the uptake of urate crystals by blood leucocytes. Others have shown that the phagocytosis of staphylococci is diminished in the presence of synovial fluid [Bodel and Hollingworth, Comparative morphology, respiration, and phagocytic function of leukocytes from blood and joint fluid in rheumatoid arthritis. J. of Clin. Invest. 45(4), 580-589 (1966)]. The phagocytosis of encapsulated Group A streptococci by human blood leucocytes was also studied in vitro by Hirsch and Church [Studies of phagocytosis of Group A Streptococci by polymorphonuclear leucocytes in vitro. J. Exp. Med. 111, 309-322 (1960)]. These workers demonstrated that the Na-HA of the capsule has antiphagocytic activity. They also determined that human, but not rabbit, serum, contains a factor which counteracts the antiphagocytic effect of the capsular Na-HA. The nature of this factor was not elucidated by them but an antibody to Na-HA or a Na—HA depolymerizing enzyme was excluded.

The stimulatory effect of Na-HA on the phagocytic activity of both mononuclear and polymorphonuclear phagocytes was recently demonstrated. Thus, Hakansson, Halgren, and Venge [Hyaluronic Acid—A New Opsonin. (Personal communication; 1978)] showed that Na-HA with a molecular weight higher than $0.7-2 \times 10^6$ in low concentration (1-10 µg/ml) stimulates the initial rate of phagocytosis of plastic beads by human blood leucocytes. This stimulatory effect is specific for serum opsonized particles. The uptake of IgG coated particles was not stimulated.

Forrester & Balazs, supra, found that phagocytosis of peritoneal machrophages is also stimulated by Na-HA at low concentrations. The mechanism of both the stimulation and inhibition for mono- and polymorphonuclear phagocytes is described in detail by Paul and Balazs in, The mechanism of the regulation of phagocytosis of human polymorphonuclear phagocytes by Na-Hyaluronate. Science (in publication, 1979).

Stossel, in Phagocytosis: Recognition and Ingestion. Seminars in Hematology, Volume 12, 83-116 (1973) ascertained that phagocytosis occurs in two phases: first, the recognition and adhesion and second, the ingestion of internalization. The stimulating effect of Na-HA in low concentrations is due to the enhanced adhesion which in turn increases the rate of ingestion. This stimulation, however, does not cause the cells to ingest more particles than they would without Na-HA. What the stimulation accomplishes is an increase in the total number of particles adhered to the cell surface at any given time. This in turn makes it possible for the rate of ingestion to be increased. That is, the cells complete their maximum level of phagocytosis during a shorter period of time. The inhibition at higher Na-HA concentrations ($>100$ µg/ml), on the other hand, does not affect the adhesion process at all, but inhibits the ingestion phase of phagocytosis. This effect is entirely dependent on the viscosity of the solution. The viscosity depends on both the concentration and molecular size. Therefore the total inhibition of phagocytosis can be achieved with a 10 mg/ml solution of Na-HA with a MW of 48,000, a 5 mg/ml solution of Na-HA, with a MW of 260,000 or with a 0.4 mg/ml solution of Na-HA with a MW of 3.2 million.

Klockars and Roberts, in Stimulation of phagocytosis by human lysozyme. Acta Haemat. 55, 289-295 (1976) found that muramidase (MUas) stimulates phagocytosis by human polymorphonuclear phagocytes. However, only homologous, i.e., human, but not egg white MUas showed this effect. The stimulation was observed in 10 to 100 µg/ml concentrations of MUas using yeast cells as the phagocyted particles. This concentration of MUas is in the same range as was found in inflammatory exudates by Senn, Chu, O'Malley and Holland, Experimental and Clinical Studies on Murmaidase (Lysozyme). Acta haemat. 44, 65-77 (1970), and in arthritic synovial fluids by Pruzanski, Ogryzlo and Katz, Lysozyme production and abnormalities in rheumatic diseases. In Lysozyme. Academic Press, New York. Chapter 38, 419-425 (1974). Klockars and Roberts, supra, suggested that MUas released by the phagocytes during the ingestion phase (see Wright and Malawista, [The mobilization and extracellular release of granular enzymes from human leukocytes during phagocytosis. J. of Cell Biology, 53, 788-798 (1972)] has an "auto-stimulatory" effect on the cells. MUas, however, is not an opsonin, because it acts on the cell membrane rather than on the particle.

SUMMARY OF THE INVENTION

The present invention provides, in one aspect thereof, novel synergistic compositions capable of stimulating both types of phagocytic and pinocytic cells, i.e., monomuclear phagocytes (MNP) and polymorphonuclear phagocytes (PNP). This aspect of the invention is based on my discovery of the fact that the known phagocytosis stimulating effect of HA can be enhanced several times by mixing with it a small amount of MUas. The synergistic effect is evident because increasing the concentration of either HA or MUas by itself does not increase the stimulating effect. Thus, by using the two substances together the stimulation of phagocytosis is elevated to a level which is not achieved by either of the two alone.

The effect of the invention is achieved when the blood concentration of MUas and Na-HA are both about 10-50 μg/ml. In order to reach that level in the blood system, a physiological saline solution containing about 5-40 mg/ml of Na-HA and about 2-20 mg/ml of MUas is used. Typically, 1-2 ml of such a solution will be injected subcutaneously or intramuscularly. Slow release of the two substances will result in the desired 10-50 μg/ml concentration in the blood.

The compositions according to the invention thus are aqueous physiological saline solutions containing pure MUas (2-20 mg/ml) and a soluble salt (preferably, the sodium salt) of hyaluronic acid (Na-HA) having a molecular weight of at least about 430,000 (the upper limit is not critical) in an amount of 5-40 mg/ml. For the stimulation of polymorphonuclear phagocytes, the most preferred blood concentration is about 10-30 μg/ml.

In another aspect thereof, the present invention provides methods of stimulating phagocytic activity by administering to an animal in need of enhanced phagocytosis, such as, for example, severe burn patients in danger of widespread infection, a therapeutically effective amount of the compositions according to the invention.

DETAILED DESCRIPTION

Before describing the invention in detail, it is expedient to describe the materials and methods that are used in carrying out the invention.

Materials And Methods

Mononuclear phagocytes (MNP)

These cells were obtained from the mouse peritoneum. Only stimulated cells were used. The stimulation was achieved by intraperitoneal injection of thioglycollate. The cells were harvested 2-3 days after the injection.

Polymorphonuclear phagocytes (PNP)

These cells were obtained from healthy male donors. They were collected and used within 2-3 hours. The serum used for coating the plastic beads was, in each case obtained from the same blood that the cells were obtained from. This method of separation of PNP from the blood is described by Ehlenberger and Nussenzweig in The role of membrane receptors for C3b and C3d in phagocytosis, J. Exp. Med. 145, 357-371 (1977).

Phagocytosis tests.

The particles used in these tests were latex beads (1.101μ diameter), obtained from Dow Diagnostics, Indianapolis, Ind. The particles were opsonized with fresh serum before use for attachment and ingestion tests in PNP.

The phagocytosis test for MNP is described in detail by Forrester and Balazs. For completeness, however that test is herein described in detail.

PHAGOCYTOSIS ASSAY

Phagocytosis by macrophage monolayers was quantitated using polystyrene latex spheres (PLS) (1.099 microndiameter) according to the method of Vassali et al. [Cell 8 1976]. The PLS were washed once in ten volumes of 70% ethanol and twice in the same volume of phosphate-buffered saline (PBS). The beads were then re-suspended in Hank's Minimum Essential Medium with 20% FCS at a concentration of $1.36 \times 10^9$ PLS/ml and kept at 4° C. until use. To each macrophage monolayer, 1 ml. of prewarmed PLS was added, and phagocytosis of the beads allowed to proceed for one hour at 37° C. in a humidified atmosphere of 95% air-5% $CO_2$. The monolayers were then thoroughly washed with PBS (6-10 times) and examined by phase contrast microscopy. All PLS were seen to be cell-associated and 85% appeared to be intracellular. Control cultures incubated at 4° C. were included in all experiments to account for particle adhesion to cell surface as opposed to true ingestion of PLS.

The cells were then lysed with 0.5 ml Triton-X 100 (Fisher Scientific, New Jersey) at a concentration of 0.05% v/v in distilled water, and the subsequent PLS suspension was diluted with 1.0 ml of 0.05% Triton-X. The absorbance of light at 540 nm through the PLS suspension was then measured. Values were corrected for background turbidity due to the presence of lysed cell-membranes which was minimal and constant. The values obtained were compared to standard curves, and the number of PLS particles ingested by a monolayer was compared in control and test conditions. In most cases the phagocytosis index ($C_E/C_O$), which is the ratio of the concentration of ingested PLS under test conditions ($C_E$) and control conditions ($C_O$), was calculated from this ratio.

In most experiments $0.5 \times 10^6$ cells were used per test and about 100-1000 plastic beads were used per cell. The incubation time varied between 1-5 hours.

The tests for adhesion and ingestion are described by Mickl, Ohlbaum and Silverstein in 2-Deoxyglucose selectively inhibits Fc and complement receptor-mediated phagocytosis in mouse peritoneal macrophages. II. Dissociation of the inhibitory effect of 2-Deoxyglucose on phagocytosis and ATP-generation. J. Exp. Med. 114,1484-1493 (1976).

Muramidase

Egg white muramidase (lysozyme) is used in this invention.

Hyaluronate

The sodium, or any other water soluble salt of hyaluronic acid can be used. The purity of the Na-HA is not critical in the present invention. Therefore, while the highly purified special fraction of Na-HA called Healon (U.S. Pat. No. 4,141,973) is preferred, other less pure commercially available preparations can be used.

The molecular weight of the Na-HA was determined by limiting viscosity number measurements using the equation $$MW = \left(\frac{[n]}{0.026}\right)^{1.25}$$

where [n] is the limiting viscosity expressed in cc/g.

Muramidase stimulation of phagocytic activity

It was shown previously (Klockars and Roberts, supra) that egg white muramidase does not stimulate human granulocyte phagocytosis because of the species specificity of this molecule. In making the present invention, I confirmed this finding as will appear below. In addition, it was also found that as far as peritoneal macrophages of rats and humans are concerned, this rule does not hold. The stimulation of phagocytosis by MUas seems to operate only at a relatively narrow concentration range, i.e., about 10–50 ug/ml (Table I below). At 100 ug/ml concentration, not only is there no stimulation, but rather, inhibition occurs.

Na-HA effect on phagocytosis

Previous, unpublished studies in my laboratory showed that the level of phagocytosis, that is, the total number of particles ingested by an MNP cannot be increased by adding Na-HA to the medium (Paul and Balazs, supra). The number of beads adhering to the cell wall and the rate of ingestion, however, can be stimulated by adding a sufficient amount of Na-HA of a molecular weight of over 300,000 to achieve a blood level of 10-100 ug/ml.

MUas, however, seems to act differently. It stimulates slightly the total amount of beads taken up by the MNP. This slight increase of phagocytosis is greatly enhanced, in accordance with the invention, when Na-HA in low concentration (10-30 ug/ml) is simultaneously added to the medium. By this is meant that sufficient Na-HA is added to achieve a blood level concentration of about 10-30 ug/ml. This stimulatory effect of Na-HA is a property only of the large molecular weight (MW 430,000 or greater) Na-HA.

It is known (Hakanson et al., supra) that Na-HA alone, without MUas, stimulates the rate of phagocytosis in PNP's. This is caused by the increased adhesion of the particles to the cell surface in the presence of Na-HA (Paul and Balazs, supra). Egg white MUas did not stimulate this phagocytosis of the human PNP. I have now, in accordance with the invention, shown that Na-HA in the presence of MUas significantly increases the level of phagocytosis (Table IV below).

EXPERIMENTS AND RESULTS

Muramidase stimulation of mononuclear phagocytes

MUas has been found to stimulate the phagocytosis of mouse or rat peritoneal macrophages This stimulation is not very dramatic (approximately 30%) but it is highly significant and moreover, does not occur at either 1 or 100 ug/ml MUas concentrations. The MUas stimulation is observed only when the cells themselves do not show an extremely high phagocytic activity. The results of these experiments are shown in Table I. From these results, it is seen that the stimulatory effect occurs at concentrations of about 10-50 ug/ml.

TABLE I.

| Stimulation of phagocytosis by MUas in mononuclear phagocytes | |
|---|---|
| MUas concentration µg/ml | Phagocytosis index |
| 1 | 0.96 ± 0.10 |
| 10 | 1.28 ± 0.04* |
| 20 | 1.32 ± 0.03* |
| 50 | 1.42 ± 0.04* |
| 100 | 0.74 ± 0.03 |

*Mean of 5-11 independent experiments, each consisting of 5 control and 5 test samples; standard deviation: 0.12.

Lack of stimulation by Na-HA

Na-HA has been found not to cause an elevation of the level of phagocytosis in MNP. That is, the phagocytosis index after 2-5 hours incubation is not different when Na-HA at low concentration (10-30 ug/ml) is present or absent in the incubation media. Varying the molecular weight of the Na-HA between 48,000 and 2,300,000 also does not make any difference. This is shown in Table II.

TABLE II.

| Phagocytosis index of mononuclear phagocytes in the presence of 10 µg/ml Na-HA of various molecular weights | |
|---|---|
| M.W. | Phagocytosis index |
| 48,000 | 0.98 ± 0.03 |
| 110,000 | 1.04 ± 0.02 |
| 260,000 | 1.01 ± 0.03 |
| 430,000 | 0.92 ± 0.03 |
| 1,300,000 | 1.02 ± 0.06 |
| 2,300,000 | 1.01 ± 0.02 |

The mean phagocytosis index is calculated from 3-5 independent experiments, each consisting of an equal number (five) of control and test samples.

Stimulation of phagocytosis of MNP by Na-HA and MUas

When Na-HA in low concentrations (10-50 ug/ml) is added to the medium which also has MUas present at a concentration of 10-50 ug/ml, the phagocytosis index increases considerably and significantly as is shown in Table III. This unexpected stimulation of the phagocytosis index occurs only if the molecular weight of the added Na-HA is about 430,000 or greater.

TABLE III.

| The effect of Na-HA and MUas mixture on phagocytosis of MNP. | | | |
|---|---|---|---|
| M.W. of Na-HA | MUas | MUas + Na-HA | Significance |
| | 1.23 ± 0.01 | 1.57 ± 0.01 | <0.001 |
| 2,300,000 | 1.25 ± 0.05 | 1.75 ± 0.01 | <0.001 |
| | 1.50 ± 0.01 | 2.03 ± 0.01 | <0.001 |
| | 1.33 ± 0.03 | 1.52 ± 0.01 | <0.001 |
| | 1.28 ± 0.01 | 1.40 ± 0.01 | <0.001 |
| | 1.14 ± 0.02 | 1.26 ± 0.01 | <0.001 |
| 1,300,000 | 1.12 ± 0.02 | 1.50 ± 0.03 | <0.001 |
| | 1.38 ± 0.02 | 1.13 ± 0.01 | NS |
| 430,000 | 1.25 ± 0.03 | 1.21 ± 0.02 | NS |
| 260,000 | 1.31 ± 0.03 | 1.33 ± 0.02 | NS |
| | 1.35 ± 0.01 | 1.38 ± 0.02 | |
| | 1.35 ± 0.03 | 1.25 ± 0.03 | |
| 110,000 | 1.11 ± 0.02 | 1.19 ± 0.05 | NS |
| | 1.38 ± 0.04 | 1.26 ± 0.04 | |
| | 1.25 ± 0.04 | 1.38 ± 0.02 | |

The stimulation of polymorphonuclear phagocytes

MUas (egg white) alone does not stimulate either the attachment or phagocytosis of human PNP. However, when Na-HA in low concentration (10-30 ug/ml) is present, both the attachment and phagocytosis are significantly enhanced as shown in Table IV.

TABLE IV

| The effect of MUas and Na—on polymorphonuclear phagocytes | | | |
|---|---|---|---|
| Na—HA µg/ml | MUas µg/ml | Attachment index | Phagocytosis index |
| 10 | — | 3.02 ± 0.03 | 1.31 ± 0.02 |
| — | 10 | 0.97 ± 0.03 | 1.01 ± 0.02 |
| 10 | 10 | 3.20 ± 0.02 | 3.02 ± 0.05 |

A WORKING HYPOTHESIS

It is clear from the foregoing that the combined use of Na-HA and MUas exerts a significantly enhanced stimulatory effect on phagocytosis. I believe that this result can be explained and therefore, for the sake of completeness, propose the following hypothesis. Of course, it is only a hypothesis and I do not wish to be bound by it in any way.

The first stage of phagocytosis requires the recognition and the subsequent attachment of the particles to the cell surface. This is achieved either by specific antigen-antibody interaction or by serum or tissue opsonins. This process does not require the metabolic activity of the cell; therefore it occurs at 4° C. and in poisoned cells. In my experiments using latex particles, the serum opsonins are essential for the recognition and attachment to the phagocytic cell surface.

Large molecular weight Na-HA has a chain conformation which provides a specific site on the molecule which interacts with a specific cell surface receptor. The Na-HA interacting with the cell surface acts as a cofactor in the attachment of the opsonized particle. Therefore in the presence of large molecular weight Na-HA more particles are attached to the surface of the cells than in the absence of it. MUas does not influence this first phase of phagocytosis.

The second phase, the ingestion (engulfment or internalization) can be triggered by MUas which is released by the phagocytic cell. This autostimulation of the cell proceeds, and the added MUas slightly stimulates the ingestion. This stimulatory effect of MUas is apparently very sensitive to the conformation of the molecule, and while human PNP need species-specific enzymes, mouse MNP can be stimulated by hen MUas. The role of Na-HA is critical in this process. Very low concentrations (10–50 ug/ml) of this molecule can significantly increase the MUas effect in MNP and cause a nearly 3-fold increase in the case of PNP. The mechanism of this effect is based on the stimulation of adhesion by Na-HA. Since more particles are on the surface of the cell, more can be incorporated into the cell. Furthermore, a cooperative binding between MUas and Na-HA on the cell surface assures that the enzyme is better bound to its substrate. I postulate that the enzymatic effect of MUas on the cell coating polysaccharide is essential for the ingestion of the particles. By adding a mixture of MUas and Na-HA, one can assure a greater attachment of particles to the cell surface and an increase in enzyme activity that is essential for ingestion.

PRACTICAL USES

The medical significance of the present invention is that in infections diseases or when the phagocytic activity is impaired (for example, in burn patients) subcutaneous or intramuscular injection or local application of Na-HA-MUas mixtures will provide a slow release of both substances to the blood circulation where the effect on the phagocytic activity of white blood cells can be stimulated. By means of normal blood circulation, the two compounds will be carried to specific locations in tissues where bacterial or sterile injury causes stress to the phagocytic system. An increase of Na-HA and MUas concentration at such locations will restore and even elevate the phagocytic activity of the cells.

Na-HA mixed with or coupled with MUas (human or animal origin) can be used. If a high concentration of Na-HA (10–30 mg/ml) in jelly form is mixed with MUas, diffusion from the injection site will be slow and a depot type of treatment is achieved. If hyaluronic acid in the above concentration is mixed with MUas, a precipitate will occur, which when suspended in 0.02–0.1 N NaCl (at pH 6.5–7.5) will form a suspension which can be injected subcutaneously or intramuscularly. The hyaluronic acid will then form a complex which slowly will dissolve under the effect of the salt solution in the intercellular space. This slow solubilization of the mixture and its slow release to the circulatory system will provide a depo-treatment.

Variations and modifications can, of course, be made without departing from the spirit and scope of the invention.

Having thus described my invention what I desire to secure by Letters Patent and hereby claim is:

1. A composition for stimulating phagocytosis, said composition comprising a physiological saline solution containing muramidase an a soluble salt of hyaluronic acid, having a molecular weight of at least about 430,000, both in amounts sufficient so that when about 1–2 ml. thereof are subcutaneously or intramuscularly injected in a mammal the concentration of each in the blood system of said mammal is about 10–50 ug/ml.

2. A composition according to claim 1, wherein the concentration of each is about 10–30 ug/ml.

3. A composition according to claim 1, wherein the solution contains about 5–40 mg of said salt of hyaluronic acid and about 2–20 mg of muramidase per 1–2 ml of saline solution.

4. A method of stimulating phagocytosis in a mammal, said method comprising administering to said mammal a therapeutically effective amount of the composition as claimed in claim 1.

5. A method of stimulating phagocytosis in a mammal, said method comprising administering to said mammal a therapeutically effective amount of the composition as claimed in claim 2.

6. A method of stimulating phagocytosis in a mammal, said method comprising administering to said mammal a therapeutically effective amount of the composition as claimed in claim 3.

* * * * *